United States Patent
Colas

(10) Patent No.: US 6,634,355 B2
(45) Date of Patent: Oct. 21, 2003

(54) SINGLE BREATH INDUCTION ANESTHESIA APPARATUS

(76) Inventor: Marie-José Colas, 1327 Bradley, Sherbrooke (CA), J1J 1M1

( * ) Notice: Subject to any disclaimer, the term of this patent is extended or adjusted under 35 U.S.C. 154(b) by 0 days.

(21) Appl. No.: 09/337,439

(22) Filed: Jun. 21, 1999

(65) Prior Publication Data

US 2002/0117174 A1 Aug. 29, 2002

(51) Int. Cl.⁷ .................. A61M 15/00; A61M 16/10
(52) U.S. Cl. ................ 128/203.12; 128/203.28; 128/205.11; 128/205.24
(58) Field of Search .................. 128/203.13, 203.12, 128/203.26, 203.27, 203.28, 205.14, 510, 205.23, 205.24, 205.11, 205.13, 205.17

(56) References Cited

U.S. PATENT DOCUMENTS

| | | | |
|---|---|---|---|
| 883,987 A | | 4/1908 | Teter |
| 912,532 A | * | 2/1909 | Brat ................ 128/205.23 |
| 1,917,958 A | * | 7/1933 | Esjbaugh ............ 128/205.24 |
| 2,099,841 A | * | 11/1937 | Connel ............. 128/205.24 |
| 2,208,633 A | | 7/1940 | Heidbrink |
| 2,791,217 A | * | 5/1957 | Iskander ........... 128/205.24 |
| 3,552,380 A | * | 1/1971 | Heldt ................. 600/532 |
| 3,717,147 A | * | 2/1973 | Flynn ............... 128/200.14 |
| 3,794,027 A | * | 2/1974 | Johnson ............ 128/203.26 |
| 3,814,092 A | * | 6/1974 | Simionescu et al. ... 128/203.12 |
| 3,850,197 A | * | 11/1974 | Ernst ................... 137/561 |
| 3,901,230 A | * | 8/1975 | Henkin ............. 128/203.12 |
| 3,973,564 A | * | 8/1976 | Carden ............. 128/205.13 |
| 4,034,753 A | * | 7/1977 | Connel ............. 128/203.26 |
| 4,051,847 A | | 10/1977 | Henkin |
| 4,088,131 A | * | 5/1978 | Elam et al. ......... 128/205.14 |
| 4,232,667 A | * | 11/1980 | Chalon et al. ...... 128/203.26 |
| 4,312,339 A | * | 1/1982 | Thompson, Sr. .... 128/205.25 |
| 4,331,140 A | * | 5/1982 | Hallsey ............. 128/204.26 |

(List continued on next page.)

FOREIGN PATENT DOCUMENTS

| | | | |
|---|---|---|---|
| DE | 171238 | * 10/1904 | ............ 128/205.24 |
| DE | 19539655 | 9/1996 | |
| EP | 714669 | 6/1996 | |
| GB | 146862 | * 2/1921 | ............ 128/205.24 |
| WO | 94/08650 | 4/1994 | |

*Primary Examiner*—Weilun Lo
*Assistant Examiner*—Joseph F. Weiss, Jr.
(74) *Attorney, Agent, or Firm*—Swabey Ogilvy Renault; Robert Mitchell

(57) ABSTRACT

A single breath induction anesthesia apparatus for anesthetizing a patient, comprises a gas delivery system for delivering at least one gas to the patient, an oxygen supply system for providing oxygen, and an oxygen/anesthesia gas supply system for mixing oxygen and at least one anesthesia gas at a preset optimum ratio sufficient to cause anesthesia of the patient with a single breath, thereby providing an oxygen/anesthesia gas mixture. The apparatus of the invention further includes a valve for providing selective gas flow communication between the oxygen supply system and the gas delivery system or between the oxygen/anesthesia gas supply system and the gas delivery system. The valve is operable for first establishing gas flow communication between the oxygen supply system and the gas delivery system to deliver oxygen to the patient and permit preoxygenation thereof, while simultaneously inhibiting gas flow communication between the oxygen/anesthesia gas supply system and the gas delivery system to allow the oxygen/anesthesia gas mixture to reach the preset optimum ratio, and thereafter establishing gas flow communication between the oxygen/anesthesia gas supply system and the gas delivery system to deliver the oxygen/anesthesia gas mixture at the preset optimum ratio to the patient and permit single breath induction anesthesia thereof, while inhibiting gas flow communication between the oxygen supply system and the gas delivery system.

20 Claims, 3 Drawing Sheets

U.S. PATENT DOCUMENTS

| | | | | |
|---|---|---|---|---|
| 4,360,018 A | * | 11/1982 | Choksi | 128/205.12 |
| 4,453,543 A | * | 6/1984 | Kohnke et al. | 128/203.28 |
| 4,489,721 A | * | 12/1984 | Ozaki et al. | 128/205.24 |
| 4,502,481 A | | 3/1985 | Christian | |
| 4,566,480 A | * | 1/1986 | Parham | 137/271 |
| 4,619,269 A | * | 10/1986 | Cutler et al. | 128/204.23 |
| 4,649,912 A | * | 3/1987 | Collins | 128/202.13 |
| 4,791,922 A | * | 12/1988 | Lindsay-cott et al. | 128/205.28 |
| 4,883,051 A | * | 11/1989 | Westenskow et al. | 128/204.21 |
| 4,905,685 A | * | 3/1990 | Olsson et al. | 128/203.12 |
| 4,951,661 A | * | 8/1990 | Sladek | 128/202.27 |
| 5,050,593 A | * | 9/1991 | Poon | 128/204.23 |
| 5,070,871 A | * | 12/1991 | Manicom | 128/205.24 |
| 5,119,810 A | * | 6/1992 | Kiske et al. | 128/204.26 |
| 5,245,996 A | * | 9/1993 | Manicom | 128/205.24 |
| 5,320,093 A | * | 6/1994 | Raemer | 128/203.12 |
| 5,396,883 A | * | 3/1995 | Knupp et al. | 128/200.14 |
| 5,398,675 A | * | 3/1995 | Henkin et al. | 128/203.12 |
| 5,411,059 A | * | 5/1995 | Sever et al. | 137/599 |
| 5,471,979 A | * | 12/1995 | Psaros et al. | 128/205.28 |
| 5,507,280 A | * | 4/1996 | Henkin et al. | 128/203.12 |
| 5,537,992 A | * | 7/1996 | Bjoernstijerna et al. | 128/203.14 |
| 5,568,910 A | | 10/1996 | Koehler et al. | |
| 5,619,986 A | * | 4/1997 | Werner et al. | 128/204.21 |
| 5,673,683 A | * | 10/1997 | Tham et al. | 128/204.22 |
| 5,678,537 A | * | 10/1997 | Bath et al. | 128/203.12 |
| 5,678,540 A | * | 10/1997 | Kock et al. | 128/205.13 |
| 5,694,924 A | * | 12/1997 | Cewers | 128/204.21 |
| 5,699,788 A | * | 12/1997 | Lekholm et al. | 128/203.12 |
| 5,701,888 A | * | 12/1997 | Tham et al. | 128/204.21 |
| 5,746,199 A | * | 5/1998 | Bayron et al. | 128/205.24 |
| 5,769,072 A | * | 6/1998 | Olsson et al. | 128/205.13 |
| 5,979,443 A | * | 11/1999 | Dingley | 128/204.28 |
| 6,006,748 A | * | 12/1999 | Hollis | 128/205.24 |
| 6,147,147 A | * | 11/2000 | Head et al. | 128/204.21 |

* cited by examiner

SINGLE BREATH INDUCTION ANESTHESIA APPARATUS

BACKGROUND OF THE INVENTION

The present invention relates to improvements in the field of anesthesia. More particularly, the invention is concerned with a single breath induction anesthesia apparatus.

When it is necessary to anesthetise a patient, it is highly desirable to pre-oxygenate the patient prior to inducing anesthesia in order to saturate the patient's blood with oxygen so as to increase the safety of a subsequent ventilation and endotracheal intubation. Pre-oxygenation of the patient is carried out by using a parallel oxygen supply and breathing system connected by means of a conduit to the anesthesia face mask affixed to the patient. Due to the complexity of such a technique, pre-oxygenation is often skipped.

In the case where pre-oxygenation is effected, while the patient is being pre-oxygenated, the doctor usually closes with his fingers the distal end of the conduit connected to an anesthesia machine and adapted to deliver an oxygen/anesthesia gas mixture to the patient, during operation of the anesthesia machine, so as to permit the anesthesia gas in the mixture to reach a preset concentration sufficient to induce anesthesia of the patient with a single breath. Since it is impossible to close with one's fingers the anesthesia gas conduit in a gas-tight manner, leaks of anesthesia gas often occur, which pollute the operating room. When the desired concentration of anesthesia gas has been reached, the oxygen conduit is disconnected from the anesthesia face mask and the anesthesia gas conduit connected thereto. During this disconnection and connection of conduits, important leaks of anesthesia gas occur, which not only further pollute the operating room but lower the concentration of anesthesia gas in the oxygen/anesthesia gas mixture delivered to the patient so that single breath induction anesthesia of the patient is considerably slowed down.

SUMMARY OF THE INVENTION

It is therefore an object of the present invention to overcome the above drawbacks and to provide a single breath induction anesthesia apparatus which readily permits pre-oxygenation of the patient and single breath induction anesthesia thereof, without causing pollution of an operating room with anesthesia gas.

In accordance with the invention, there is thus provided a single breath induction anesthesia apparatus for anesthetizing a patient comprising: a gas delivery system for delivering at least one gas to said patient from a valve, said valve alternately providing selective gas flow communication between said gas delivery system and one of a first and a second gas flow circuit connected thereto, said first and second gas flow circuits each enabling independent gas flow therethrough; said first gas flow circuit comprising an oxygen supply system for providing oxygen to said patient, said oxygen supply system having a first oxygen inlet connected to a first oxygen source; said second gas flow circuit comprising an oxygen/anesthesia gas supply system for mixing oxygen, independently fed thereto from a second oxygen source without interrupting oxygen flow provided by said oxygen supply system from said first oxygen source to said patient, and at least one anesthesia gas at a preset optimum ratio to provide an oxygen/anesthesia gas mixture, said oxygen/anesthesia gas supply system permitting continuous circulatory flow of said oxygen/anesthesia gas mixture while oxygen from said second oxygen source and said anesthesia gas are additionally supplied thereto to ensure circulation of said oxygen/anesthesia gas mixture at said preset optimum ratio within said oxygen/anesthesia gas supply system sufficient to, when released to said gas delivery system, induce anesthesia of said patient with a single breath; and said valve including a single, flow diverting valve member movable between a first position and a second position, said first position providing gas flow communication between said oxygen supply system and said gas delivery system to deliver oxygen from said first oxygen source to said patient, thereby permitting pre-oxygenation thereof while simultaneously inhibiting gas flow communication between said oxygen/anesthesia gas supply system and said gas delivery system, and said second position providing gas flow communication between said oxygen/anesthesia gas mixture at said preset optimum ratio to said patient, thereby permitting single breath induction anesthesia of said patient while inhibiting gas flow communication between said oxygen supply system and said gas delivery system.

According to a preferred embodiment, the valve comprises a valve body having a first port in gas flow communication with the oxygen supply system, a second port in gas flow communication with the oxygen/anesthesia gas supply system and a third port in gas flow communication with the gas delivery system, and a valve member within the valve body. The valve member is movable between a first position whereat the first port is in gas flow communication with the third port and the second port is closed, and a second position whereat the first port is closed and the second port is in gas flow communication with the third port. Preferably, the valve body has first, second and third tubular branches, the first, second and third ports being defined at respective proximal ends of the first, second and third tubular branches, respectively.

According to another preferred embodiment, the second and third ports are disposed along a first axis and the first port is disposed along a second axis extending transversely of the first axis. The valve body has a generally T-shaped configuration with the second and third tubular branches extending along the first axis and the first tubular branch extending along the second axis. In such an embodiment, the valve member preferably has a T-shaped gas passage formed therein.

According to a further preferred embodiment, the valve includes stop means for arresting the movement of the valve member at each of the first and second positions. Preferably, the stop means each comprise cooperating abutment means disposed on the valve member and the valve body.

According to yet another preferred embodiment, the first tubular branch is provided with oxygen vent means for venting excess oxygen when the valve member is in the second position. Preferably, the oxygen vent means comprise an oxygen vent orifice formed in the wall of the first tubular branch and a removable closure member for selectively closing the oxygen vent orifice when the valve member is in the first position or opening the oxygen vent orifice when the valve member is in the second position.

Due to the provision of the aforesaid valve enabling selective gas flow communication between the oxygen supply system and the gas delivery system or between the oxygen/anesthesia gas supply system and the gas delivery system, the apparatus according to the invention permits pre-oxygenation of a patient and single breath induction anesthesia thereof, without causing pollution of the operating room with anesthesia gas.

BRIEF DESCRIPTION OF THE DRAWINGS

Further features and advantages of the invention will become more readily apparent from the following description of a preferred embodiment thereof as illustrated by way of example in the accompanying drawings, in which.

DESCRIPTION OF PREFERRED EMBODIMENTS

Figure 1:
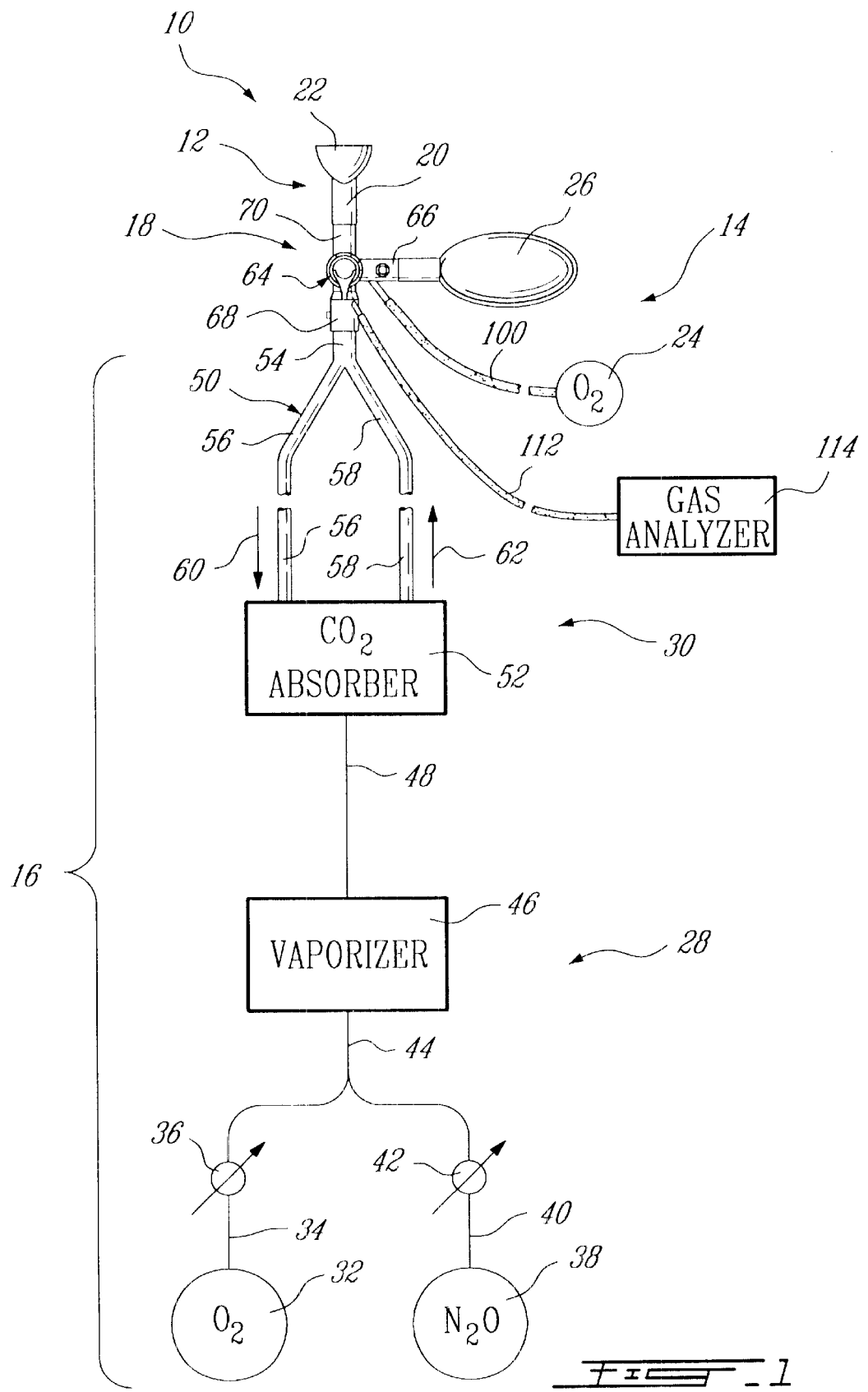
FIG. 1 schematically illustrates a single breath induction anesthesia apparatus according to a preferred embodiment of the invention.

Referring first to FIG. 1, there is illustrated a single breath induction anesthesia apparatus which is generally designated by reference numeral 10 and seen to comprise a gas delivery system 12 for delivering at least one gas to a patient (not shown), an oxygen supply system 14, an oxygen/anesthesia gas supply system 16 and a valve 18 for providing selective gas flow communication between the oxygen supply system 14 and the gas delivery system 12 or between the oxygen/anesthesia gas supply system 16 and the gas delivery system 12. The gas delivery system 12 comprises a connector tube 20 and an anesthesia face mask 22 connected thereto. The oxygen supply system 14 comprises an oxygen source 24 and an oxygen bag 26 defining an oxygen reservoir. The oxygen/anesthesia gas supply system 16, on the other hand, includes an oxygen/anesthesia gas source circuit 28 and a breathing circuit 30 in gas flow communication with one another.

The oxygen/anesthesia gas source circuit 28 comprises an oxygen source 32 for supplying oxygen which flows through line 34 provided with a valve 36 and a flow-meter (not shown), a nitrous oxide source 38 for supplying nitrous oxide which flows through line 40 provided with a valve 42 and a flow-meter (not shown), lines 34 and 40 merging into line 44, and a vaporizer 46 which is connected to line 44 and mixes the oxygen and nitrous oxide with an anesthesia gas such as sevoflurane at a preset optimum ratio sufficient to induce anesthesia of the patient with a single breath. The nitrous oxide is another anesthesia gas which increases the anesthesia effect of sevoflurane. The vaporizer is controlled so as to provide a mixture containing oxygen, nitrous oxide and sevoflurane in which the sevoflurane is present in a concentration of about 8 vol. %. The breathing circuit 30 which is in gas flow communication with the oxygen/anesthesia gas source circuit 28 via line 48 comprises a Y-shaped conduit 50 and a carbon dioxide absorber 52 connected thereto, the Y-shaped conduit 50 comprising three conduit sections 54, 56 and 58. The conduit sections 56 and 58 are provided with one-way valves (not shown) so as to direct the flow of gases exhaled by the patient through expiratory conduit section 56 along the direction indicated by arrow 60 and through inspiratory conduit section 58 along the direction indicated by arrow 62. Thus, when the valve 18 is operated to establish gas flow communication between the oxygen/anesthesia gas supply system 16 and the gas delivery system 12, gases inhaled and exhaled by the patient pass through the gas delivery system 12 and the valve 18 and circulate through the breathing circuit 30. The carbon dioxide absorber 52 absorbs carbon dioxide from the gases exhaled by the patient, thereby allowing the oxygen/anesthesia gas mixture to be returned to the patient with less carbon dioxide.

Figure 2:
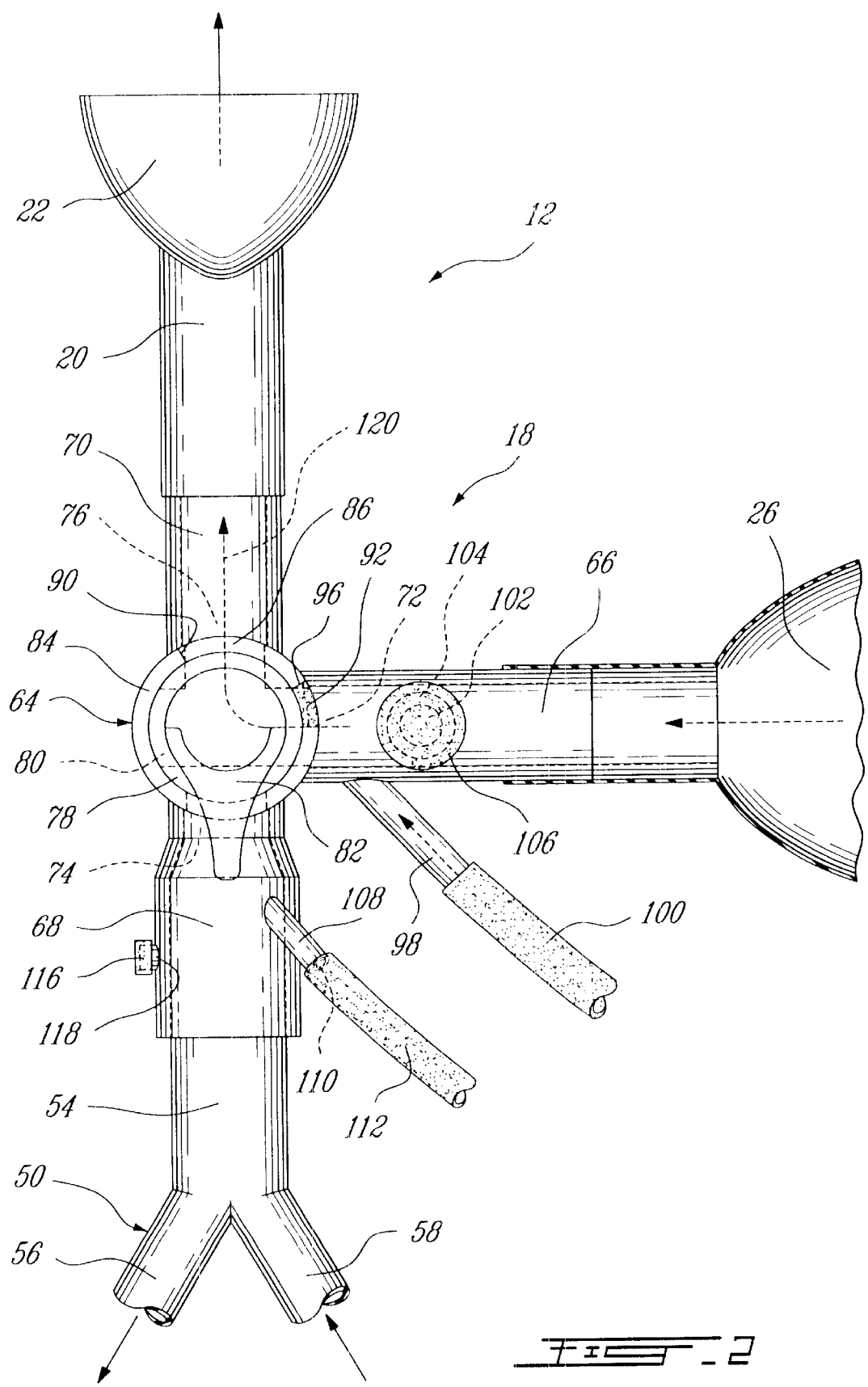
FIG. 2 is a fragmentary side view of the apparatus illustrated in FIG. 1, showing the valve with the valve member thereof in a first position.
Figure 3:
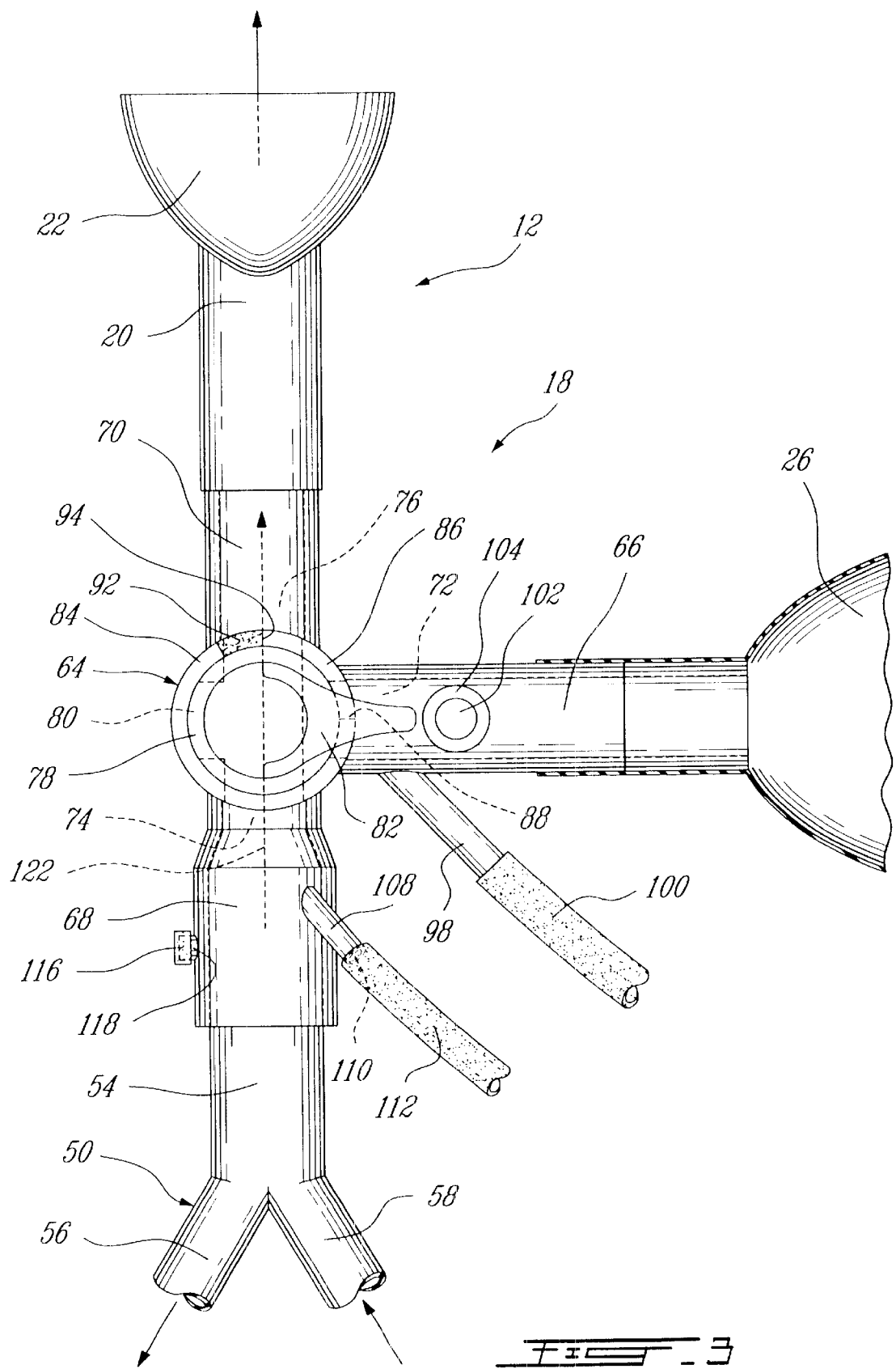
FIG. 3 is another fragmentary side view of the apparatus illustrated in FIG. 1, showing the valve with the valve member thereof in a second position.

As shown in FIGS. 2 and 3, the valve 18 is a manually operated three-way valve comprising a generally T-shaped valve body 64 having three tubular branches 66, 68 and 70 with ports 72, 74 and 76 defined at the respective proximal ends of the tubular branches 66, 68 and 70, respectively, and a valve member 78 arranged within the valve body 64 at the intersection of the tubular branches 66, 68 and 70. The valve member 78 has a T-shaped gas passage 80 formed therein and is movable between a first position shown in FIG. 2, whereat the port 72 is in gas flow communication with the port 76 and the port 74 is closed, and a second position shown in FIG. 3, whereat the port 72 is closed and the port 74 is in gas flow communication with the port 76. A handle 82 is provided for manually moving the valve member 78 between these two positions. The valve body 64 has a cylindrical portion 84 provided with an arcuate cut-out defining at the longitudinal ends thereof two abutment surfaces 88 (shown in FIG. 3) and 90 (shown in FIG. 2). The valve member 78, on the other hand, is provided with an arcuate stop member 92 extending into the cut-out 86 and having two abutment surfaces 94 (shown in FIG. 3) and 96 (shown in FIG. 2). The abutment surfaces 88 and 94 cooperate with one another to arrest the movement of the valve member 78 at the first position, whereas the abutment surfaces 90 and 96 cooperate with one another to arrest the movement of the valve member 78 at the second position.

The tubular branch 66 has a gas inlet 98 connected by means of a conduit 100 to the oxygen source 24 shown in FIG. 1, for providing gas flow communication between the port 72 and the oxygen source 24. The tubular branch 66 is also connected at its distal end to the oxygen reservoir bag 26 for providing gas flow communication between the port 72 and the oxygen reservoir bag 26. An oxygen vent orifice 102 having a annular flange 104 is formed in the wall of the tubular branch 66 for venting excess oxygen when the valve member 78 is in the second position. A removable closure member 106 is provided for selectively closing the oxygen vent orifice 102 when the valve member 78 is in the first position or opening the oxygen vent orifice 102 when the valve member 78 is in the second position.

The tubular branch 68 is connected to the conduit section 54 of the Y-shaped conduit 50 for providing gas flow communication between the port 74 and the oxygen/anesthesia gas supply system 16. Such a tubular branch is provided with a gas outlet 108 having a gas discharge orifice 110. The gas outlet 108 is connected by means of a conduit 112 to a gas analyzer 114 (shown in FIG. 1) to permit gas flow communication between the port 74 and the gas analyzer for gas analysis of the oxygen/anesthesia gas mixture. A removable closure member 116 is provided for closing the gas discharge orifice 110 when the gas analyzer is not used and the conduit 112 is disconnected from the gas outlet 108. The tubular branch 68 is also provided with a support member 118 for holding the closure member 116 when the gas outlet 108 is connected to the gas analyzer 114.

The tubular branch 70 is connected to the tube 20 for providing gas flow communication between the port 76 and the gas delivery system 12.

The tubular branches 66, 68 and 70 each have a circular cross-section with inner and outer diameters selected so that the tubular branch 66 can be fitted to any standard oxygen reservoir bag 26, the tubular branch 68 to any standard breathing circuit 30 and the tubular branch 70 to any standard gas delivery system 12.

In operation, the anesthesia face mask 22 is affixed to the patient with the valve member 78 of the valve 18 being in the position shown in FIG. 2 and the oxygen vent orifice 102 closed with the closure member 106. In this position of the valve member 78, the port 72 is in gas flow communication with the port 76 and the port 74 is closed. The oxygen source 24 is opened to allow oxygen to flow through the conduit 100, the gas inlet 98, the valve 18 along the direction indicated by arrow 120 and the gas delivery system 12, the oxygen also filling the reservoir bag 26. This permits a pre-oxygenation of the patient. The oxygen reservoir bag 26 enables the patient to inhale a larger volume of oxygen. At the same time, valves 36 and 42 are opened to allow oxygen and nitrous oxide to flow via lines 34,40,44 from the oxygen and nitrous oxide sources 32,38 to the vaporizer 46 where the oxygen and nitrous oxide are mixed with the sevoflurane contained in the vaporizer 46, the resulting gas mixture flowing from the vaporizer 46 to the breathing circuit 30 via line 48. When the sevoflurane has reached the desired concentration indicated by the gas analyzer 114, the valve member 78 of the valve 18 is moved to the position shown in FIG. 3. In this position of the valve member 78, the port 72 is closed and the port 74 is in gas flow communication with the port 76. The oxygen/anesthesia gas mixture thus flows from the oxygen/anesthesia gas supply system 16 through the valve 18 along the direction indicated by arrow 122 and the gas delivery system 12. This permits single breath induction anesthesia of the patient. The closure member 106 is removed to open the oxygen vent orifice 102 so as to allow venting of excess oxygen. Valves 36 and 42 are then partially closed to reduce the flow of oxygen and nitrous oxide.

Instead of using sevoflurane, it is possible to use any other type of anesthesia gas available on the market. The optimum concentration of anesthesia gas sufficient to cause anesthesia of a patient with a single breath may of course vary depending on the patient and the type of anesthesia gas used. The use of nitrous oxide is also optional.

Although a breathing circuit 30 of recirculatory type has been illustrated, it is possible to use other types of breathing circuits or systems, such as Mapleson systems, including Bain and Ayers T systems.

I claim:

1. A single breath induction anesthesia apparatus for anesthetizing a patient, comprising:
    a gas delivery system for delivering at least one gas to said patient from a valve, said valve alternately providing selective gas flow communication between said gas delivery system and one of a first and a second gas flow circuit connected thereto, said first and second gas flow circuits each enabling independent gas flow therethrough;
    said first gas flow circuit comprising an oxygen supply system for providing oxygen to said patient, said oxygen supply system having a first oxygen inlet connected to a first oxygen source;
    said second gas flow circuit comprising an oxygen/anesthesia gas supply system for mixing oxygen, independently fed thereto from a second oxygen source without interrupting oxygen flow provided by said oxygen supply system from said first oxygen source to said patient, and at least one anesthesia gas at a preset optimum ratio to provide an oxygen/anesthesia gas mixture, said oxygen/anesthesia gas supply system permitting continuous circulatory flow of said oxygen/anesthesia gas mixture while oxygen from said second oxygen source and said anesthesia gas are additionally supplied thereto to ensure circulation of said oxygen/anesthesia gas mixture at said preset optimum ratio within said oxygen/anesthesia gas supply system sufficient to, when released to said gas delivery system, induce anesthesia of said patient with a single breath; and
    said valve including a single, flow diverting valve member movable between a first position and a second position, said first position providing gas flow communication between said oxygen supply system and said gas delivery system to deliver oxygen from said first oxygen source to said patient, thereby permitting pre-oxygenation thereof while simultaneously inhibiting gas flow communication between said oxygen/anesthesia gas supply system and said gas delivery system, and said second position providing gas flow communication between said oxygen/anesthesia gas supply system and said gas delivery system to deliver said oxygen/anesthesia gas mixture at said preset optimum ratio to said patient, thereby permitting single breath induction anesthesia of said patient while inhibiting gas flow communication between said oxygen supply system and said gas delivery system.

2. An apparatus as claimed in claim 1, wherein said valve comprises a valve body having a first port in gas flow communication with said oxygen supply system, a second port in gas flow communication with said oxygen/anesthesia gas supply system and a third port in gas flow communication with said gas delivery system, and a valve member within said valve body, and wherein said valve member assumes said first position, said first port is in gas flow communication with said third port and said second port is closed, whereas when said valve member assumes said second position, said first port is closed and said second port is in gas flow communication with said third port.

3. An apparatus as claimed in claim 2, wherein said valve is a manually operated two-way valve.

4. An apparatus as claimed in claim 2, wherein said oxygen/anesthesia gas supply system includes a breathing circuit for collecting and recirculating gases exhaled by said patient, whereby when said valve member is in said second position gases inhaled and exhaled by said patient pass through said gas delivery system and said valve and circulate through said breathing circuit.

5. An apparatus as claimed in claim 4, wherein said breathing circuit is provided with a carbon dioxide absorber for absorbing carbon dioxide from the gases exhaled by said patient, thereby allowing said oxygen/anesthesia gas mixture to be returned to said patient with less carbon dioxide.

6. An apparatus as claimed in claim 2, wherein said valve body has first, second and third tubular branches, and wherein said first, second and third ports are defined at respective proximal ends of said first, second and third tubular branches, respectively, relative to said valve body.

7. An apparatus as claimed in claim 6, wherein said second and third ports are disposed along a first axis and said first port is disposed along a second axis extending transversely of said first axis, and wherein said valve body has a generally T-shaped configuration with said second and third tubular branches extending along said first axis and said first tubular branch extending along said second axis.

8. An apparatus as claimed in claim 7, wherein said valve member has a T-shaped gas passage formed therein.

9. An apparatus as claimed in claim 6, wherein said oxygen supply system includes an oxygen source and wherein said first tubular branch has a gas inlet connected to said oxygen source for providing gas flow communication between said first port and said oxygen source.

10. An apparatus as claimed in claim 9, wherein said oxygen supply system further includes an oxygen reservoir and wherein said first tubular branch is connected to said oxygen reservoir for providing gas flow communication between said first port and said oxygen reservoir.

11. An apparatus as claimed in claim 10, wherein said gas inlet is disposed between the proximal end of said first tubular branch and a distal end thereof, and wherein said oxygen reservoir is connected to the distal end of said first tubular branch.

12. An apparatus as claimed in claim 6, wherein said first tubular branch is provided with oxygen vent means for venting excess oxygen when said valve member is in one of said second positions, wherein said oxygen vent means consist of an oxygen vent orifice opening to the atmosphere.

13. An apparatus as claimed in claim 12, wherein said first tubular branch has a peripheral wall, said oxygen vent orifice being defined in said peripheral wall.

14. An apparatus as claimed in claim 6, wherein said second tubular branch is provided with a gas outlet having a gas discharge orifice and a removable closure member for selectively closing said gas discharge orifice or opening said gas discharge orifice to permit connection of said gas outlet to a gas analyzer and gas flow communication between said second port and said gas analyzer for gas analysis of said oxygen/anesthesia gas mixture.

15. An apparatus as claimed in claim 2, wherein said valve includes stop means for arresting a movement of said valve member at each of said first and second positions.

16. An apparatus as claimed in claim 15, wherein said stop means each comprise cooperating abutment means disposed on said valve member and said valve body.

17. An apparatus as claimed in claim 15, wherein said valve member is provided with a handle for manually moving said valve member between said first and second positions.

18. An apparatus as claimed in claim 1, wherein said anesthesia gas is sevoflurane.

19. An apparatus as claimed in claim 18, wherein said oxygen/anesthesia gas mixture at said preset optimum ratio contains sevoflurane in a concentration of about 8 vol. %.

20. An apparatus as claimed in claim 1, wherein said oxygen/anesthesia gas supply system comprises a source of oxygen, a source of sevoflurane and a source of nitrous oxide, and is adapted to provide a mixture containing oxygen, sevoflurane and nitrous oxide in which sevoflurane is present in a concentration of about 8 vol. %.

* * * * *